United States Patent
Patel et al.

(10) Patent No.: US 11,207,297 B2
(45) Date of Patent: Dec. 28, 2021

(54) LIQUID PHARMACEUTICAL COMPOSITION OF CLONIDINE

(71) Applicant: SYRI LTD, Middlesex (GB)

(72) Inventors: Kamlesh Patel, Middlesex (GB); Sanjaykumar Maganbhai Patel, Vadodara (IN); Viral Mahendrabhai Patel, Vadodara (IN)

(73) Assignee: SYRI LTD., Middlesex (GB)

( * ) Notice: Subject to any disclaimer, the term of this patent is extended or adjusted under 35 U.S.C. 154(b) by 0 days.

(21) Appl. No.: 16/312,325

(22) PCT Filed: Jun. 12, 2017

(86) PCT No.: PCT/IB2017/053458
§ 371 (c)(1),
(2) Date: Dec. 21, 2018

(87) PCT Pub. No.: WO2018/002751
PCT Pub. Date: Jan. 4, 2018

(65) Prior Publication Data
US 2019/0231749 A1   Aug. 1, 2019

(30) Foreign Application Priority Data
Jun. 28, 2016 (GB) .................................. 1611175.9

(51) Int. Cl.
*A61K 31/4168* (2006.01)
*A61K 9/08* (2006.01)
*A61K 9/00* (2006.01)
*A61P 9/12* (2006.01)
*A61K 9/12* (2006.01)

(52) U.S. Cl.
CPC ........ *A61K 31/4168* (2013.01); *A61K 9/0053* (2013.01); *A61K 9/0095* (2013.01); *A61K 9/08* (2013.01); *A61P 9/12* (2018.01)

(58) Field of Classification Search
CPC .............. A61K 31/4168; A61K 9/0053; A61K 9/0095; A61K 9/08; A61P 9/12
See application file for complete search history.

(56) References Cited

U.S. PATENT DOCUMENTS

| 2005/0058696 A1* | 3/2005 | Donello ............... A61K 31/135 424/449 |
| 2014/0093578 A1 | 4/2014 | Ketan et al. |

FOREIGN PATENT DOCUMENTS

| WO | 2011075617 A | 6/2011 |
| WO | 2015076821 A1 | 5/2015 |

OTHER PUBLICATIONS

Mohan, CalBiochem Buffers, 2003, Merck, pp. 1-37 (Year: 2003).*
Written Opinion in corresponding PCT Application No. PCT/IB2017/053458, dated Sep. 15, 2017.
International Search Report in corresponding PCT Application No. PCT/IB2017/053458, dated Sep. 15, 2017.
International Preliminary Report on Patentability in corresponding PCT Application No. PCT/IB2017/053458, dated Jan. 1, 2019.
De Goede et al., "Development and validation of a paediatric oral formulation of clonidine hydrochloride", International Journal of Pharmaceutics, vol. 433, pp. 119-120 (2012) (in English; cited in counterpart UK Appl. No. GB1611175.9 and Australian Appl. No. 2017291464).
Office Action, dated Mar. 23, 2017, issued in counterpart UK Appl. No. GB1611175.9 (in English, 6 pages).
Office Action, dated Jul. 4, 2017, issued in counterpart UK Appl. No. GB1611175.9 (in English, 4 pages).
Office Action, dated Nov. 20, 2020, issued in counterpart Australian Appl. No. 2017291464 (in English, 4 pages).

* cited by examiner

*Primary Examiner* — Sarah Pihonak
(74) *Attorney, Agent, or Firm* — Westerman, Hattori, Daniels and Adrian, LLP

(57) ABSTRACT

The present invention relates to liquid pharmaceutical composition suitable for oral administration comprising clonidine or pharmaceutically acceptable salts thereof with at least one buffer and at least one preservative. The present invention also relates to process for preparing the said liquid pharmaceutical composition.

14 Claims, No Drawings

LIQUID PHARMACEUTICAL COMPOSITION OF CLONIDINE

CROSS-REFERENCE TO RELATED PATENT APPLICATIONS

This application is a U.S. National Stage Application under 35 U.S.C. § 371 of International Patent Application No. PCT/IB2017/053458, filed 12 Jun. 2017, which claims the benefit of priority under 35 U.S.C. Section 119(e) of British Patent Application number GB 1611175.9 filed 28 Jun. 2016, all of which are incorporated by reference in their entireties. The International Application was published on 4 Jan. 2018, as International Publication No. WO 2018/002751 A1.

FIELD OF THE INVENTION

The present invention contemplates liquid pharmaceutical composition. The present invention contemplates more particularly to the liquid pharmaceutical composition of clonidine or pharmaceutically acceptable salts thereof suitable for oral administration.

BACKGROUND OF THE INVENTION

Clonidine is chemically known as N-(2,6-dichlorophenyl)-4,5-dihydro-1H-imidazol-2-amine and can be represented as below structure;

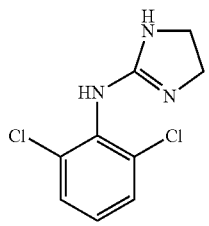 [SMILES: Clc1cccc(Cl)c1NC1=NCCN1]

Clonidine was disclosed in U.S. Pat. No. 3,454,701 which is incorporated herein as reference. Clonidine is known since very long and widely used as alpha-adrenergic agonist. Clonidine is an α-adrenergic receptor agonist that exhibits affinity for central presynaptic α2 receptors in the sympathetic nervous system. Clonidine is known to be effective in the treatment of a many clinical disorders including hypertension; Tourette's syndrome; prophylaxis of common migraine headaches; and decreasing hyperactivity, impulsivity and over excitability in Attention Deficit Hyperactivity Disorder, manic states and many other clinical syndromes.

The commercially available clonidine products are in the form of hydrochloride salt as Catapres® in tablet form for oral administration in three dosage strengths: 0.1 mg, 0.2 mg and 0.3 mg and contains Lactose monohydrate, Calcium hydrogen phosphate (anhydrous), Maize starch, dried Colloidal silica (anhydrous), Povidone, Soluble starch and Stearic acid indicated for treatment of all grades of essential and secondary hypertension. Another commercially available product is Dixarit® in the form of tablet in 25 microgram dosage strength indicated for prophylactic management of migraine or recurrent vascular headache and management of vasomotor conditions commonly associated with the menopause and characterised by flushing and contains Calcium hydrogen phosphate anhydrous, Lactose monohydrate, Maize starch, Colloidal anhydrous silica, Povidone, Maize starch soluble, Indigo carmine (E132) and Magnesium stearate in tablet core and Povidone, Sucrose, Talc, Acacia, Titanium dioxide (E171), Indigo carmine (E132), Macrogol, Carnauba wax and White beeswax. Few more formulations of Clonidine are available in the market as transdermal patch (Catapres-TTS), or as an injectable form to be given epidurally, directly to the central nervous system.

Commercially available oral dosage form is administered three to four times a day or via a transdermal patch. After oral administration, clonidine is almost completely absorbed from the gastrointestinal tract and is subject to rapid liver metabolism. A peak plasma level is generally reached within 3 to 5 hours and the plasma half-life is about 12 to about 16 hours and has an elimination half-life of about 6 to about 24 hours.

In pharmaceutical formulation, major market is covered by solid oral formulations or dosage forms because of ease of manufacturing, storage, stability etc. However on the other hand, there are a huge number of patients who have difficulties swallowing like children and aged people and few patients with mental disorder or nauseated and there are certain situation when patient is travelling and have very little or no access of water. In all such cases, the solid formulations appears to be non viable and may result in patient non compliance and medication error or discontinuation of medication.

In absence of any oral liquid formulation available in the market, hospitals & dispensaries generally follows practice of preparing extemporaneous suspensions from available solid formulation and triturating the same followed by adding water and if required with syrup to make it palatable. For clonidine also such practice is followed by crushing commercially available tablet formulation and mixing with water and syrup or some sweetener to prepare palatable oral suspension for patient. (http://napra.ca/Content_Files/Files/Manitoba/UpdateClonidine5mcg-mLSyrup.pdf).

Pharmacy practice of dispensing extemporaneous suspensions from solid formulation can creates medication error and fatal conditions especially for the drug which falls in low therapeutic index. In case of clonidine itself many cases of clonidine toxicities or overdoses has been reported as per references provided below;

1) Oral Clonidine Suspension: 1000-Fold Compounding Errors Cause Harm to Children ISMPCSB2011-01-ClonidineSusp.
2) Romano M J, Dinh A. A 1000-fold overdose of clonidine caused by a compounding error in a 5-year-old child with attention deficit/hyperactivity disorder. Paediatrics. 2001; 108(2):471-473.
3) Farooqi M F, Seifert S A, Kunkel S J, Johnson M I, Benson B E. Toxicity from a clonidine suspension. J Med Toxicol. 2009; 5(3):130-133.
4) Suchard J R, Graeme J R. Paediatric clonidine poisoning as a result of pharmacy compounding error. Pediatr Emerg Care. 2002:18(4):295-296.
5) Anderson R J, Hart G R, Crumpler C P, Lerman M J. Clonidine overdose: report of six cases and review of the literature. Ann Emerg Med. 1981; 10(2):107-112.

Thus following the practice of extemporaneous suspensions dispensing for low therapeutic index drug is very unsafe and fatal for life.

To overcome such situation oral liquid formulation is required. In case of liquid formulations widely known and used formulations are in the form of solution and/or suspension. Suspension formulation further offers many drawbacks of physical stability issues like sedimentation and compaction, difficulty in formulation development, uniform and accurate dosing is challenge. In reference to clonidine overdose references mentioned above, the majority pharmaceutical formulations prepared were in the form of suspensions which resulted in medication error or overdose.

CN104523683 describes clonidine hydrochloride dry suspension comprises 40-90 parts of clonidine hydrochloride, 500-2000 parts of a filler, 50-180 parts of a corrigent, 40-100 parts of a suspending aid and 10-40 parts of a flocculant.

US2014093578 and WO2015076821 discloses the dosage unit comprising a pharmaceutically effective amount of a coated complex comprising clonidine bound to a cationic exchange resin, which is characterized by a twenty-four hour release profile with a single peak, wherein said oral clonidine dosage unit provides a therapeutically effective plasma concentration for at least about 70%, or at least 85% of the twenty-four hour period following the single dose administration.

US2008152709 describes pharmaceutical composition comprising clonidine or a pharmaceutically acceptable salt or prodrug thereof. The composition, when administered to a patient in an amount delivering a clonidine dose of about 0.1 to about 2 mg/day, exhibits clonidine release properties providing a 24-hour profile of plasma clonidine concentration that (a) does not substantially or protractedly fall below about 0.2 ng/ml and exhibits a peak concentration that is therapeutically effective and does not cause unacceptable side effects in the patient; and/or (b) exhibits a peak that substantially coincides with or closely anticipates a time of maximum plasma concentration of a catecholamine occurring in a diurnal cycle of a patient having a catecholamine-mediated disease or disorder.

WO9622768 discloses an extended release formulation as solid oral dosage unit comprising a homogenous mixture of clonidine, one or more cellulose ethers, and one or more therapeutically inert, pharmaceutically accepted fillers.

Still there is a need exists in the society for liquid pharmaceutical formulation of clonidine which overcome all the problems discussed above and suitable for oral administration without any stability or dose uniformity issue. Inventors of the present invention have addressed these issues and provided liquid pharmaceutical composition suitable for oral administration comprising clonidine or pharmaceutically acceptable salts thereof.

SUMMARY OF THE INVENTION

The main aspect of the present invention is to provide a liquid pharmaceutical composition suitable for oral administration comprising clonidine or pharmaceutically acceptable salts thereof present in the range from about 0.0005 to about 0.002% w/v, at least one buffer and at least one preservative.

Another aspect of the present invention is to provide a liquid pharmaceutical composition suitable for oral administration comprising clonidine or pharmaceutically acceptable salts thereof present in the range from about 0.0005 to about 0.002% w/v, at least one buffer, wherein buffer strength is in the range from 5 to 25 millimolar at least one preservative present in the range from 0.001% w/v to about 0.5% w/v and wherein the composition is having pH in the range from 4-7.

Yet another aspect of the present invention is to provide liquid pharmaceutical composition of clonidine or pharmaceutically acceptable salts thereof for treatment of all grades of essential and secondary hypertension, prophylactic management of migraine or recurrent vascular headache and management of vasomotor conditions associated with the menopause and characterised by flushing.

One more aspect of the present invention is to provide process for preparing the liquid pharmaceutical composition of clonidine or pharmaceutically acceptable salts thereof.

DETAILED DESCRIPTION OF THE INVENTION

Liquid pharmaceutical composition of clonidine or pharmaceutically acceptable salts thereof suitable for oral administration is the invention as further described herein.

The main embodiment of the invention is a liquid pharmaceutical composition suitable for oral administration comprising clonidine or pharmaceutically acceptable salts thereof, at least one buffer and at least one preservative.

The term "pharmaceutically-acceptable salts" as used herein includes salts commonly used to form alkali metal salts and to form addition salts of free acids or free bases. Suitable pharmaceutically-acceptable acid addition salts of clonidine may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, alginic, $\beta$-hydroxybutyric, malonic, galactaric and galacturonic acid. Suitable pharmaceutically-acceptable base addition salts of clonidine include metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. In a preferred embodiment, clonidine or a pharmaceutically acceptable salts present in the liquid pharmaceutical composition as clonidine hydrochloride. In one embodiment the Clonidine hydrochloride is present in the range from about 0.0005% w/v to about 0.002% w/v, preferably in the range from about 0.008% w/v to about 0.0012% w/v.

The term "about" as and where used in this specification means $\pm 10\%$ of the mentioned value. However when the term "about" is used in connection with pH, it should be considered as $\pm 2$ unit of the pH value.

To keep liquid pharmaceutical composition of present invention stable for longer period of time, the pH may be maintained such that the composition is acidic or neutral. As per one embodiment, pH of the composition should be in the range from about 4 to 7, preferably in the range from about 5 to 6.

The liquid pharmaceutical composition of the present invention is chemically and physically stable without any precipitation or crystallization during stability study and further overcame problem of unpleasant taste.

Further liquid pharmaceutical compositions of the present invention show a suitable stability and reproducibility.

The liquid pharmaceutical composition of present invention being in the form of solution also offers an advantage of clear colourless formulation, uniform dosing, no physical stability problem and also offers very less chances of medication error or over dosage. The liquid pharmaceutical composition of the present invention, as described herein remains stable in at least 80% purified water.

As per one embodiment, the liquid pharmaceutical composition of the present invention comprises clonidine or pharmaceutically acceptable salts thereof and preservative and buffer.

In one embodiment, suitable preservative for present invention can be selected from methyl parahydroxybenzoate (methyl paraben), ethyl parahydroxybenzoate (ethyl paraben), propyl parahydroxybenzoate (propyl paraben), butyl parahydroxybenzoate (butyl paraben), isobutyl parahydroxybenzoate (isobutyl paraben), isopropyl parahydroxybenzoate (isopropyl paraben), benzyl parahydroxybenzoate (benzyl paraben), Sodium Benzoate, Benzoic acid, Potassium Sorbate and combinations thereof. In one embodiment the preservative is present in the range from about 0.001% w/v to about 0.5% w/v.

In one embodiment, suitable buffer for present invention is selected from Citric Acid, Sodium Citrate, Sodium Dihydrogen Phosphate, Disodium Phosphate, Trometamol (Tris), Hydrochloric Acid, Ascorbic Acid, Sodium Ascorbate and anhydrous, monohydrate or dehydrate forms thereof. Further the buffer can be single or any combination of above listed buffer. In a preferred embodiment, combination of Sodium Dihydrogen Phosphate and Disodium Phosphate is to be used. Buffer used for present invention is having buffer strength in range from 5 to 150 millimolar. Further as per preferred embodiment the buffer strength is in the range from 5 to 25 millimolar.

As per another embodiment the liquid pharmaceutical composition may further comprises sweetener.

In one embodiment, suitable sweetener for present invention is selected from acesulfame potassium, sucralose, cyclamate, saccharin, saccharin sodium and aspartame or mixtures thereof. In a preferred embodiment, sucralose is to be used. The liquid pharmaceutical composition of the present invention can be prepared in absence of sweetener. However to make it more palatable and easily acceptable by patient especially children, very small amount of sweetener can be added. Sweetener for the present invention can be used in the range from about 0.00% w/v to 0.5% w/v.

As per one more embodiment, the liquid pharmaceutical composition may further comprise anti oxidants.

In one embodiment, suitable antioxidants for present invention can be selected from the group consisting of butylated hydroxyanisole (BHA), butylated hydroxytoluene (BHT), ascorbic acid, beta-carotene, alpha-tocopherol, propyl gallate, gentisic acid sodium ascorbate, sodium bisulfite, sodium metabisulfite, monothioglycero, cysteine, thioglycolate sodium, acetone sodium bisulfite, ascorbate (sodium/acid), bisulfite sodium, cystein/cysteinate HCl, dithionite sodium (Na hydrosulfite, Na sulfoxylate), gentisic acid, gentisic acid ethanolamine, glutamate monosodium, formaldehyde sulfoxylate sodium, metabisulfite potassium, metabisulfite sodium, monothioglycerol (thioglycerol), propyl gallate, sulfite sodium, tocopherol alpha, thioglycolate sodium or the mixtures thereof.

Further as one embodiment the liquid formulation of present invention, vehicle or solvent is selected from glycerine, alcohols, propylene glycol, polyethylene glycol, water, ethanol, isopropyl alcohol or their mixtures thereof. Preferably purified water is used as a solvent. In one embodiment, the liquid pharmaceutical composition of present invention comprise at least 80% the vehicle or purified water, preferably at least 90%, more preferably at least 95% and most preferably at least 99% of total composition.

Thus as per one embodiment, the liquid pharmaceutical composition of present inventions remain stable at different temperature conditions even in presence of at least 80% of purified water in to the composition.

One more embodiment of the present invention is to provide a liquid pharmaceutical composition suitable for oral administration comprising clonidine or pharmaceutically acceptable salts thereof, at least one buffer, wherein buffer strength is in the range from 5 to 25 millimolar, at least one preservative present in the range from 0.001% w/v to about 0.5% w/v and wherein the composition is having pH in the range from 4-7.

According to an embodiment of the present invention, said liquid pharmaceutical composition suitable for oral administration comprises;
 a) 0.0005 to 0.002% w/v of clonidine hydrochloride,
 b) 0.001 to 0.5% w/v of preservative and
 c) buffer having buffer strength of 5 to 150 millimolar
 d) 0.00 to 0.5% w/v of sweetener.

One another embodiment of the present invention, said liquid pharmaceutical composition suitable for oral administration comprises;
 a) 0.001% w/v of clonidine hydrochloride,
 b) 0.180% w/v of Methyl parahydroxybenzoate and
 c) sodium dihydrogen phosphate and Disodium phosphate having total buffer strength of 5 to 25 millimolar Yet another embodiment of the present invention, said liquid pharmaceutical composition suitable for oral administration comprises;
 a) 0.001% w/v of clonidine hydrochloride,
 b) 0.180% w/v of Methyl parahydroxybenzoate,
 c) sodium dihydrogen phosphate and Disodium phosphate having total buffer strength of 5 to 25 millimolar
 d) 0.04% w/v of sucralose.

As per one embodiment of the present invention, the liquid pharmaceutical composition of present invention is prepared by process comprising steps of
 a) adding preservative in purified water,
 b) adding buffer,
 c) optionally adding sweetener,
 d) adding clonidine or pharmaceutically acceptable salts thereof and
 e) adding purified water to make up to final volume and ensuring pH between 5.0 to 6.0.

As per one embodiment dosage of clonidine in liquid composition of present invention is in the range from 2 mcg/ml to 50 mcg/ml. In a preferred embodiment, the dosage is in the range form 2 mcg/ml to 20 mcg/ml.

As per another embodiment of the present invention the liquid pharmaceutical composition of clonidine is to be advised to administer in dosage of 100 mcg to 150 mcg per day. In a preferred embodiment, the liquid pharmaceutical composition of clonidine is advised to administer as 5 ml of composition twice a day or thrice a day.

As per one more embodiment of the present invention the liquid pharmaceutical composition of clonidine or pharmaceutically acceptable salts thereof is to be used for treatment of hypertension; Tourette's syndrome; prophylaxis of common migraine headaches; and decreasing hyperactivity, impulsivity and over excitability in Attention Deficit Hyperactivity Disorder, manic states and many other clinical syndromes.

As per preferred embodiment of the present invention the liquid pharmaceutical composition of clonidine or pharmaceutically acceptable slats thereof is to be used for for treatment of all grades of essential and secondary hypertension, prophylactic management of migraine or recurrent vascular headache and management of vasomotor conditions associated with the menopause and characterised by flushing.

The invention is further illustrated by the following examples, which are by no means intended to limit the scope of the invention but are given by way of illustration.

EXAMPLES

Example 1: Clonidine Hydrochloride Solution (10 Mcg/Ml)

| Ingredients | gm/100 ml |
|---|---|
| Clonidine hydrochloride | 0.001 gm |
| Methyl parahydroxybenzoate | 0.180 gm |
| Sodium dihydrogen phosphate monohydrate | 0.200 gm |
| Disodium phosphate, anhydrous | 0.010 gm |
| Sucralose | 0.040 gm |
| Purified water | Up to 100 ml |

Manufacturing Process:
1. Methyl parahydroxybenzoate was added in to small portion of purified water with heating at about 90° C. and later kept aside to cool at room temperature.
2. Sodium dihydrogen phosphate monohydrate and Disodium hydrogen phosphate anhydrous were added to solution of step 1) and mixed to get clear colourless solution.
3. Sucralose was added to solution of step 2) by mixing to get a clear, colourless solution.
4. Clonidine hydrochloride was added to solution of step 3) and mixed to get a clear, colourless solution.
5. Purified water was added to solution of step 4) and mixed to get a clear, colourless solution.
6. pH of the solution was checked to ensure it is be between 5.0 to 6.0.

Example 2: Clonidine Hydrochloride Solution (20 Mcg/Ml)

| Ingredients | gm/100 ml |
|---|---|
| Clonidine hydrochloride | 0.002 gm |
| Methyl parahydroxybenzoate | 0.180 gm |
| Sodium dihydrogen phosphate monohydrate | 0.200 gm |
| Disodium phosphate, anhydrous | 0.010 gm |
| Sucralose | 0.040 gm |
| Purified water | Up to 100 ml |

Manufacturing process: As per Example 1

Example 3: Clonidine Hydrochloride Solution (5 Mcg/Ml)

| Ingredients | gm/100 ml |
|---|---|
| Clonidine hydrochloride | 0.0005 gm |
| Methyl parahydroxybenzoate | 0.180 gm |
| Sodium dihydrogen phosphate monohydrate | 0.200 gm |
| Disodium phosphate, anhydrous | 0.010 gm |
| Purified water | Up to 100 ml |

Manufacturing process: As per Example 1 except sucralose was not added.

Example 4: Stability Studies

Stability study of composition of Example 1 was performed at different temperature and relative humidity conditions for 3 months and results are as described below;

| | Method | Initial | 3 months @ 2-8° C. | 3 months @ 25° C. | 3 months @ 40° C. |
|---|---|---|---|---|---|
| Description | Ph. Eur. 2.2.1 & 2.2.2 | Clear Colourless solution | Clear Colourless solution | Clear Colourless solution | Clear Colourless solution |
| pH | In-house (PH meter) | 5.67 | 5.68 | 5.68 | 5.67 |
| Assay (%) | In-house (HPLC) | 100.74 | 100.35 | 100.24 | 100.21 |
| Density (Gm/ml) | In-house | 0.9994 | 0.9997 | 0.9997 | 0.9998 |
| Impurity | | | | | |
| Single max unknown | In-house (HPLC) | BLQ | 0.247 | 0.253 | 0.252 |
| Total impurities | | BLQ | 0.247 | 0.253 | 0.252 |

Thus after 3 months exposure to extreme temperature condition like 40° C., the liquid pharmaceutical composition of clonidine hydrochloride remains stable without any potency reduction or increase in impurity.

The invention claimed is:
1. A liquid pharmaceutical solution suitable for oral administration, consisting of:
   clonidine or pharmaceutically acceptable salts thereof present in the amount of 0.001% w/v,
   at least one buffer having a buffer strength in the range from 5 to 150 millimolar,
   at least one sweetener, and
   at least one preservative in purified water,
   wherein the solution has a pH in the range from 5 to 6.
2. The liquid pharmaceutical solution according to claim 1, wherein the at least one buffer is selected from the group consisting of Citric Acid, Sodium Citrate, Sodium Dihydrogen Phosphate, Disodium Phosphate, Trometamol (Tris), Hydrochloric Acid, Ascorbic Acid, Sodium Ascorbate anhydrous, monohydrate forms thereof, and dehydrate forms thereof, either singly or in combination.
3. The liquid pharmaceutical solution according to claim 2, wherein the at least one buffer is a combination of Sodium Dihydrogen Phosphate and Disodium Phosphate.
4. The liquid pharmaceutical solution according to claim 1,
   wherein the preservative is selected from the group consisting of methyl parahydroxybenzoate (methyl paraben), ethyl parahydroxybenzoate (ethyl paraben), propyl parahydroxybenzoate (propyl paraben), butyl parahydroxybenzoate (butyl paraben), isobutyl parahydroxybenzoate (isobutyl paraben), isopropyl parahydroxybenzoate (isopropyl paraben), benzyl parahydroxybenzoate (benzyl paraben), Sodium Benzoate, Benzoic acid, Potassium Sorbate, and combinations thereof, and
   wherein the preservative is present in the range from 0.001% w/v to about 0.5% w/v.

5. The liquid pharmaceutical solution according to claim 1, wherein the at least one sweetener is selected from the group consisting of acesulfame potassium, sucralose, cyclamate, saccharin, saccharin sodium, aspartame, and mixtures thereof.

6. A liquid pharmaceutical solution suitable for oral administration, consisting of:
   clonidine or pharmaceutically acceptable salts thereof present in the amount of 0.001% w/v,
   a combination of sodium dihydrogen phosphate and disodium phosphate,
   at least one buffer having a buffer strength in the range from 5 to 25 millimolar,
   at least one sweetener, a pharmaceutically acceptable solvent or vehicle, and
   methyl paraben present in the range from 0.001% w/v to about 0.5% w/v,
   wherein the solution has a pH in the range from 5 to 6.

7. The liquid pharmaceutical solution according to claim 1, wherein the buffer strength of the at least one buffer is in the range from 5 to 25 millimolar.

8. The liquid pharmaceutical solution according to claim 4, wherein the preservative is methyl paraben.

9. The liquid pharmaceutical solution according to claim 5, wherein the at least one sweetener is sucralose.

10. A liquid pharmaceutical solution suitable for oral administration according to claim 6,
    wherein the clonidine is clonidine hydrochloride, and
    wherein the at least one sweetener is present in the range of from 0.001 to 0.5% w/v.

11. The liquid pharmaceutical solution according to claim 1, wherein the solution is prepared by a process comprising:
    adding a preservative to purified water,
    adding a buffer having a buffer strength in the range from 5 to 150 millimolar,
    adding a sweetener,
    adding clonidine or pharmaceutically acceptable salt thereof, and
    adding purified water to make up to a final volume and such that the liquid pharmaceutical solution has a pH in the range from 5 to 6.

12. The liquid pharmaceutical solution according to claim 11,
    wherein the preservative is methyl paraben,
    wherein the buffer comprises sodium dihydrogen phosphate and disodium phosphate,
    wherein the buffer strength of the at least one buffer is in the range from 5 to 25 millimolar, and
    wherein the sweetener is sucralose.

13. A method of treating a disease, comprising:
    orally administering the liquid pharmaceutical solution according to claim 1 to a patient in need of treatment of the disease wherein the disease is selected from hypertension, Tourette's syndrome, migraine headaches or recurrent vascular headache, attention deficit hyperactivity disorder, manic states, and vasomotor conditions associated with menopause and characterized by flushing.

14. The method of treating a disease according to claim 13,
    wherein the buffer strength of the at least one buffer is in the range from 5 to 25 millimolar.

* * * * *